(12) United States Patent
Gross et al.

(10) Patent No.: US 7,635,345 B2
(45) Date of Patent: *Dec. 22, 2009

(54) PRESSURE-PROPELLED SYSTEM FOR BODY LUMEN

(75) Inventors: Yossi Gross, Moshav Mazor (IL); Oz Cabiri, Macabim (IL); Boris Degtiar, Modl'In (IL); Eran Shor, Moshav Bizaron (IL)

(73) Assignee: G. I. View Ltd., Ramat Gan (IL)

( * ) Notice: Subject to any disclaimer, the term of this patent is extended or adjusted under 35 U.S.C. 154(b) by 723 days.

This patent is subject to a terminal disclaimer.

(21) Appl. No.: 10/838,648

(22) Filed: May 3, 2004

(65) Prior Publication Data

US 2005/0154355 A1    Jul. 14, 2005

Related U.S. Application Data

(63) Continuation-in-part of application No. 10/753,424, filed on Jan. 9, 2004.

(51) Int. Cl.
    *A61M 29/00* (2006.01)
(52) U.S. Cl. .................................. 604/99.01
(58) Field of Classification Search ......... 604/523–539, 604/264, 96.01, 101.01–5, 102.01–3, 916, 604/917, 920, 921, 99.01; 606/191–194
    See application file for complete search history.

(56) References Cited

U.S. PATENT DOCUMENTS

| | | | |
|---|---|---|---|
| 3,895,637 A | 7/1975 | Choy | |
| 3,924,625 A | 12/1975 | Peterson | |
| 4,040,413 A | 8/1977 | Ohshiro | |
| 4,066,070 A | 1/1978 | Utsugi | |
| 4,077,610 A | 3/1978 | Masuda | |
| 4,148,307 A | 4/1979 | Utsugi | |
| 4,176,662 A | 12/1979 | Frazer | |
| 4,327,722 A * | 5/1982 | Groshong et al. | ........... 604/510 |
| 4,403,985 A | 9/1983 | Boretos | |
| 4,530,698 A | 7/1985 | Goldstein et al. | |
| 4,561,427 A | 12/1985 | Takada | |
| 4,596,381 A | 6/1986 | Hamrick | |

(Continued)

FOREIGN PATENT DOCUMENTS

EP    0242428    10/1987

(Continued)

OTHER PUBLICATIONS

U.S. Appl. No. 60/490,038.

(Continued)

*Primary Examiner*—Manuel A Mendez
(74) *Attorney, Agent, or Firm*—Ladas & Parry LLP (57) ABSTRACT

Apparatus is provide for use with a fluid pressure source, including an elongate carrier, adapted to be inserted through a proximal opening of a body lumen, and a distal piston head coupled to a distal portion of the carrier. The piston head is adapted to be in direct contact with a wall of the lumen when the carrier is inserted into the lumen, and to be advanced distally through the body lumen in response to pressure from the fluid pressure source. Additionally, the piston head is typically adapted to facilitate passage of fluid out of the lumen from a site within the lumen distal to the piston head.

36 Claims, 6 Drawing Sheets

U.S. PATENT DOCUMENTS

| | | |
|---|---|---|
| 4,690,131 A | 9/1987 | Lyddy et al. |
| 4,838,859 A | 6/1989 | Strassmann |
| 4,971,034 A | 11/1990 | Doi et al. |
| 4,976,524 A | 12/1990 | Chiba |
| 5,259,364 A | 11/1993 | Bob et al. |
| 5,337,732 A | 8/1994 | Grundfest et al. |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A * | 3/1995 | Ortiz et al. ............... 600/114 |
| 5,471,988 A | 12/1995 | Fujio et al. |
| 5,509,371 A | 4/1996 | Phillips |
| 5,571,114 A | 11/1996 | Devanaboyina |
| 5,586,968 A | 12/1996 | Grundl et al. |
| 5,604,531 A | 2/1997 | Iddan et al. |
| 5,662,587 A | 9/1997 | Grundfest et al. |
| 5,728,068 A | 3/1998 | Leone et al. |
| 5,740,808 A | 4/1998 | Panescu et al. |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,157,018 A | 12/2000 | Ishiguro et al. |
| 6,277,065 B1 | 8/2001 | Donofrio |
| 6,296,608 B1 | 10/2001 | Daniels et al. |
| 6,315,713 B1 | 11/2001 | Takada |
| 6,332,865 B1 | 12/2001 | Begg et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi |
| 6,517,477 B1 | 2/2003 | Wendlandt |
| 6,527,705 B1 | 3/2003 | Ouchi |
| 6,537,206 B2 | 3/2003 | Takada |
| 6,544,216 B1 | 4/2003 | Sammler et al. |
| 6,597,520 B2 | 7/2003 | Wallerstein et al. |
| 6,599,237 B1 | 7/2003 | Singh |
| 6,611,282 B1 | 8/2003 | Trubko et al. |
| 6,648,814 B2 | 11/2003 | Kim et al. |
| 6,682,479 B1 | 1/2004 | Takahashi et al. |
| 6,695,771 B2 | 2/2004 | Takada |
| 6,702,734 B2 | 3/2004 | Kim et al. |
| 6,702,735 B2 | 3/2004 | Kelly |
| 6,704,148 B2 | 3/2004 | Kumata |
| 6,709,388 B1 | 3/2004 | Mosse et al. |
| 6,743,208 B1 | 6/2004 | Coyle |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler |
| 6,911,005 B2 | 6/2005 | Ouchi et al. |
| 6,932,323 B2 | 8/2005 | James |
| 6,974,441 B2 | 12/2005 | Ravo |
| 7,056,283 B2 | 6/2006 | Baror et al. |
| 2002/0012059 A1 | 1/2002 | Wallerstein et al. |
| 2002/0072651 A1 | 6/2002 | Vilos |
| 2002/0107478 A1 | 8/2002 | Wendlandt |
| 2002/0109772 A1 | 8/2002 | Kuriyama et al. |
| 2002/0109773 A1 | 8/2002 | Kuriyama et al. |
| 2003/0000526 A1 | 1/2003 | Gobel |
| 2003/0074015 A1 | 4/2003 | Nakao |
| 2003/0083547 A1 | 5/2003 | Hamilton et al. |
| 2003/0105386 A1 | 6/2003 | Voloshin et al. |
| 2003/0168068 A1 | 9/2003 | Poole et al. |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0143161 A1 | 7/2004 | Baror et al. |
| 2004/0199087 A1 | 10/2004 | Swain et al. |
| 2004/0199088 A1 | 10/2004 | Bakos et al. |
| 2004/0199196 A1 | 10/2004 | Ravo |
| 2004/0204702 A1 | 10/2004 | Ziegler et al. |
| 2004/0249247 A1 | 12/2004 | Iddan |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0085841 A1 | 4/2005 | Eversull et al. |
| 2005/0095200 A1 | 5/2005 | Schwarzberg |
| 2005/0107664 A1 | 5/2005 | Kalloo et al. |
| 2005/0154355 A1 | 7/2005 | Gross et al. |
| 2005/0165272 A1 | 7/2005 | Okada et al. |

FOREIGN PATENT DOCUMENTS

| | | |
|---|---|---|
| EP | 0267446 | 5/1988 |
| EP | 0659387 | 6/1995 |
| FR | 1465723 | 3/1967 |
| JP | 7-313443 | 12/1995 |
| JP | 2006026344 | 2/2006 |
| WO | WO 00/44275 | 8/2000 |
| WO | WO 01/68540 | 9/2001 |
| WO | WO 02/059676 | 8/2002 |
| WO | WO 02/075348 | 9/2002 |
| WO | WO 03/026272 | 3/2003 |
| WO | WO 03/045487 | 6/2003 |
| WO | WO 03/046830 | 6/2003 |
| WO | WO 03/053225 | 7/2003 |
| WO | WO 2004/010858 | 2/2004 |
| WO | WO 2004/016299 | 2/2004 |
| WO | WO 2004/069057 | 8/2004 |
| WO | WO 2006/025045 | 3/2006 |

OTHER PUBLICATIONS

U.S. Appl. No. 10/753,424, filed Jan. 9, 2004, Applicant Yosef Gross, and Office Action of Apr. 14, 2008.

English abstract of JP 2006026344 dated Feb. 2, 2006.

* cited by examiner

PRESSURE-PROPELLED SYSTEM FOR BODY LUMEN

CROSS-REFERENCES TO RELATED APPLICATIONS

The present application is a continuation-in-part (CIP) of U.S. patent application Ser. No. 10/753,424 to Gross et al., entitled, "Pressure-propelled system for body lumen," filed Jan. 9, 2004, which is incorporated herein by reference.

FIELD OF THE INVENTION

The present invention relates generally to a pressure-propelled system, suitable for imaging body lumens, such as the gastrointestinal (GI) tract.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like. In a conventional method of examining a colon using an endoscope, for example, the endoscope is typically manually inserted into the colon. In this manual technique, patients may often complain of abdominal pain and distention because the colon is extended or excessively dilated, thereby necessitating stopping the endoscopic procedure. Furthermore, it is not unusual for the colon to bleed and be accidentally perforated. Insertion of an endoscope through the sigmoid colon and into the descending colon, or through the splenic flexure, the transverse colon, the hepatic flexure or parts affected by previous operations may also be accompanied with difficulty. Because of these reasons, a colonoscopy is typically performed by a relatively small number of skilled practitioners, and the rate of patient pain and discomfort is high.

U.S. Pat. No. 5,337,732 to Grundfest et al., whose disclosure is incorporated herein by reference, describes a robot for performing endoscopic procedures, which includes a plurality of segments attached to each other through an articulated joint. Actuators can move the segments together and apart and change their angular orientation to allow the robot to move in an inchworm or snake-like fashion through a cavity or lumen within a patient. Inflatable balloons around the segments inflate to brace a temporarily stationary segment against the lumen walls while other segments move. A compressed gas line attached to the back segment provides compressed gas to inflate the balloons and optionally to drive the actuators. The lead segment includes a television camera and biopsy arm or other sensors and surgical instruments.

U.S. Patent Application Publication 2003/0168068 to Poole and Young, whose disclosure is incorporated herein by reference, describes a method for lining a body cavity with a liner that contains two chambers by (a) selectively controlling fluid pressure in a first of the chambers so as cause the first chamber to evert and advance into said body cavity, and (b) selectively controlling fluid pressure in a second of said chambers to control the stiffness of the liner.

U.S. Patent Application Publication 2003/0105386 and U.S. Pat. No. 6,485,409 to Voloshin et al., whose disclosures are incorporated herein by reference, describe endoscopic apparatus comprising an inflatable sleeve, wherein inflating the sleeve causes an endoscope to be advanced into the colon.

U.S. Patent Application Publication 2002/0107478 to Wendlandt, whose disclosure is incorporated herein by reference, describes a self-propelled catheter, wherein pressurizing an everting tube coupled to the catheter advances the catheter into the body.

U.S. Pat. No. 6,702,735 to Kelly, whose disclosure is incorporated herein by reference, describes a device for moving a tool along a passage. The tool is coupled to an inflatable sheath, such that as the sheath is inflated it extends into the passage and carries the tool along.

U.S. Pat. No. 5,259,364 to Bob, et al., whose disclosure is incorporated herein by reference, describes an endoscopic device comprising a flexible eversion tube, wherein inflating the eversion tube causes an endoscope to be advanced into a body cavity.

U.S. Pat. No. 4,403,985 to Boretos, whose disclosure is incorporated herein by reference, describes a catheter containing ports near its distal end through which high pressure fluid is forced to advance and steer the catheter.

SUMMARY OF THE INVENTION

Some embodiments of the present invention provide an imaging system which is propelled by fluid pressure through a body lumen, such as the gastrointestinal (GI) tract. Embodiments of the invention are described hereinbelow with reference to the GI tract, but it is understood that these embodiments are not limited to use in the GI tract, and may be used for other body lumens as well. Unlike the prior art, which may inflate and anchor balloons and similar devices to the GI tract wall in an attempt to overcome the low friction of the GI tract, these embodiments of the present invention utilize the very low friction environment of the GI tract to propel the imaging system, typically with no need for anchoring.

There is thus provided, in accordance with an embodiment of the present invention, a system including a guide member at least partially insertable into a proximal opening of a body lumen, the guide member including a first passageway connectable to a source of fluid pressure, an elongate carrier arranged for sliding movement through the guide member, and a piston head mounted on the carrier, wherein a greater fluid pressure acting on a proximal side of the piston head than on a distal side of the piston head propels the piston head and the carrier in a distal direction in the body lumen.

The system of this embodiment of the invention may have different features. For example, the piston head may be inflatable. The carrier may include a second passageway in fluid communication with the piston head, which may be connected to a source of fluid pressure for inflating the piston head. A vent tube may pass through the piston head, having an opening distal to the piston head through which fluid may be vented to the outside. An image-capturing device may be mounted on the carrier, such as distal to the piston head. A power supply tube may pass through the carrier and may be connected to the image-capturing device. A fluid supply tube may pass through the carrier and may be connected to a fluid source.

In accordance with an embodiment of the present invention, an auxiliary piston head may be mounted on the carrier proximal to the first-mentioned piston head. The auxiliary piston head, which may be inflatable, may be fixed axially to the carrier at a fixed or variable distance from the first-mentioned piston head. The carrier may include a third passageway in fluid communication with the auxiliary piston head, which may be connected to a source of fluid pressure for inflating the auxiliary piston head.

There is therefore provided, in accordance with an embodiment of the present invention, apparatus for use with a biologically-compatible-fluid pressure source, including:

an elongate carrier, adapted to be inserted through a proximal opening of a body lumen; and a distal piston head coupled to a distal portion of the carrier and adapted to:
be in direct contact with a wall of the lumen when the carrier is inserted into the lumen,
be advanced distally through the body lumen in response to pressure from the fluid pressure source, and
facilitate passage of fluid out of the lumen from a site within the lumen distal to the piston head.

In an embodiment, an outer surface of the piston head in contact with the wall of the lumen includes a low friction coating suitable for facilitating sliding of the piston head against the wall of the lumen.

In an embodiment, the lumen includes a gastrointestinal (GI) tract, and the piston head is adapted to be in direct contact with a wall of the GI tract when the carrier is inserted into the GI tract. For example, the GI tract may include a colon, and the piston head may be adapted to be in direct contact with a wall of the colon when the carrier is inserted into the colon.

In an embodiment, the apparatus includes a vent tube, and the piston head is adapted to facilitate the passage of the fluid out of the lumen through the vent tube. For some applications, the vent tube is shaped to define an inner diameter thereof that is between 1 and 3 millimeters. In an embodiment, the vent tube is adapted to passively permit the passage of the fluid out of the lumen. Alternatively, the vent tube is adapted to be coupled to a suction source, whereby to actively facilitate the passage of the fluid out of the lumen. For example, the vent tube may be adapted to be coupled to the suction source such that during operation of the apparatus, a pressure distal to the piston head is between −5 millibar and +15 millibar.

In an embodiment, the piston head is adapted to be inflated so as to attain and maintain the direct contact with the wall of the colon.

For some applications:
(i) the apparatus includes an auxiliary piston head, coupled to the carrier at a position proximal to the distal piston head,
(ii) the auxiliary piston head is adapted to be inflated so as to attain and maintain direct contact with the wall of the colon, and
(iii):
(a) at at least one time while the carrier is within the body lumen, the distal piston head is adapted to be in a state of being already deflated at least in part simultaneously with the auxiliary piston head being already inflated and being advanced distally through the colon in response to pressure from the fluid pressure source, and
(b) at at least one other time while the carrier is within the body lumen, the auxiliary piston head is adapted to be in a state of being already deflated at least in part simultaneously with the distal piston head being already inflated and being advanced distally through the colon in response to pressure from the fluid pressure source.

In an embodiment, the piston head is adapted to be intermittently deflated at least in part, while in the colon, whereby to facilitate the passage of the fluid out of the lumen from the site within the lumen distal to the piston head.

In an embodiment, the apparatus includes a piston-head-pressure sensor, adapted to sense a pressure within the piston head. Alternatively or additionally, the apparatus includes a distal pressure sensor, adapted to sense a pressure within the colon distal to the piston head. Further alternatively or additionally, the apparatus includes a proximal pressure sensor, adapted to sense a pressure within the colon proximal to the piston head. For some applications, one, two, or three of these sensors are provided.

In an embodiment, the apparatus includes:
a pressure sensor, adapted to measure a first pressure associated with operation of the apparatus; and
a control unit, adapted to regulate a second pressure associated with operation of the apparatus responsive to the measurement of the pressure sensor.

For example, the pressure sensor may be adapted to measure a pressure selected from the list consisting of: a pressure distal to the piston head, a pressure proximal to the piston head, and a pressure within the piston head.

In an embodiment, the control unit is adapted to regulate the pressure being measured by the pressure sensor. Alternatively, the control unit is adapted to regulate a pressure other than that being measured by the pressure sensor.

In an embodiment, the piston head is shaped to define a proximal lobe and a distal lobe, the lobes being in fluid communication with each other.

For some applications:
(a) a volume of a first one of the lobes is adapted to decrease in response to a constriction of the colon adjacent thereto,
(b) a volume of a second one of the lobes is adapted to remain constant in the absence of a change in colon diameter adjacent thereto, even if the volume of the first lobe is decreased, and/or
(c) a pressure within the first and second lobes is equal in steady state, regardless of the decrease in volume of the first lobe.

In an embodiment, the piston head is adapted to be at an inflation pressure between 10 and 60 millibar during advancement through the colon (e.g., 20-50 millibar, or 30-45 millibar). Alternatively or additionally, the piston head is adapted to advance through the colon in response to a pressure from the fluid pressure source that is between 30% and 100% of the inflation pressure. For example, the piston head may be adapted to advance through the colon in response to a pressure from the fluid pressure source that is between 50% and 100% of the inflation pressure (e.g., between 50% and 80% of the inflation pressure).

In an embodiment, the piston head is shaped to define a distally-narrowing portion, and is adapted to be inserted into the colon such that a tip of the distally-narrowing portion points in a distal direction when the piston head is in the colon. For some applications, a proximal base of the distally-narrowing portion has a characteristic fully-inflated diameter that is larger than a diameter of at least a part of the colon through which the distally-narrowing portion is adapted to pass, whereby the base of the distally-narrowing portion does not inflate fully when the base is in that part of the colon.

There is further provided, in accordance with an embodiment of the present invention, a method, including:
placing a distal piston head in direct contact with a wall of a body lumen;
applying fluid pressure to the distal piston head to advance the piston head distally through the body lumen; and
facilitating passage of fluid out of the lumen from a site within the lumen distal to the piston head.

In an embodiment, the method includes applying a low friction coating to an outer surface of the piston head intended for contact with the wall of the lumen, the low friction coating being suitable for facilitating sliding of the piston head against the wall of the lumen.

In an embodiment, the lumen includes a gastrointestinal (GI) tract, and placing the piston head includes placing the piston head in direct contact with a wall of the GI tract. In an embodiment, the GI tract includes a colon, and placing the piston head includes placing the piston head in direct contact with a wall of the colon.

In an embodiment, facilitating the passage of the fluid includes facilitating the passage of the fluid out of the lumen through a vent tube extending from the site distal to the piston head to a site outside of the lumen. For some applications, facilitating the passage of the fluid includes passively permitting the passage of the fluid through the vent tube and out of the lumen. Alternatively, facilitating the passage of the fluid includes actively removing the fluid from the lumen. For example, actively removing the fluid may include applying to the site distal to the piston head a pressure between −5 millibar and +15 millibar.

In an embodiment, placing the piston head in direct contact with the wall includes inflating the piston head to an extent sufficient to attain and maintain the direct contact with the wall of the colon.

In an embodiment, the method includes:

placing an auxiliary piston head proximal to the distal piston head;

inflating the auxiliary piston head to an extent sufficient to attain and maintain direct contact with the wall of the colon;

at at least one time while the distal piston head is within the body lumen, deflating the distal piston head at least in part, such that at a post-distal-piston-head-deflation time when the distal piston head is in a state of being already deflated at least in part, the auxiliary piston head is inflated and advancing distally through the colon in response to the applied fluid pressure; and at at least one other time while the distal piston head is within the body lumen, deflating the auxiliary piston head at least in part, such that at a post-auxiliary-piston-head-deflation time when the auxiliary piston head is in a state of being already deflated at least in part, the distal piston head is inflated and advancing distally through the colon in response to the applied pressure.

In an embodiment, facilitating the passage of the fluid out of the lumen includes intermittently deflating the piston head at least in part.

In an embodiment, the method includes sensing a pressure within the piston head, within the colon distal to the piston head, and/or within the colon proximal to the piston head.

In an embodiment, the method includes:

sensing a first pressure associated with performing the method; and regulating a second pressure associated with performing the method, responsive to sensing the first pressure.

For example, sensing the first pressure may include sensing a pressure selected from the list consisting of: a pressure distal to the piston head, a pressure proximal to the piston head, and a pressure within the piston head.

For some applications, regulating the second pressure includes regulating the first pressure. Alternatively, regulating the second pressure does not include regulating the first pressure.

In an embodiment, inflating the piston head includes inflating the piston head at an inflation pressure between 10 and 60 millibar. Alternatively or additionally, applying the fluid pressure includes setting the fluid pressure to between 30% and 100% of the inflation pressure (e.g., between 50% and 100% of the inflation pressure, or between 50% and 80% of the inflation pressure).

In an embodiment, inflating the piston head includes inflating the piston head at an inflation pressure between 20 and 50 millibar (e.g., between 30 and 45 millibar).

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
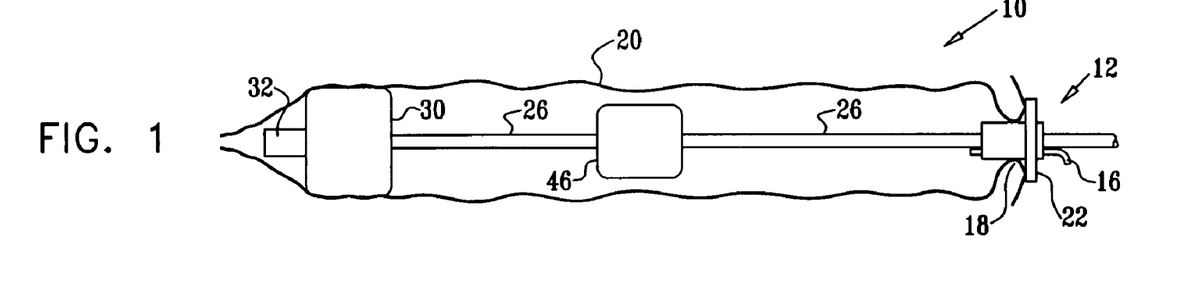
FIG. 1 is a simplified pictorial illustration of a system, constructed and operative in accordance with an embodiment of the present invention, which may be suitable for imaging body lumens, such as the GI tract.
Figure 2:
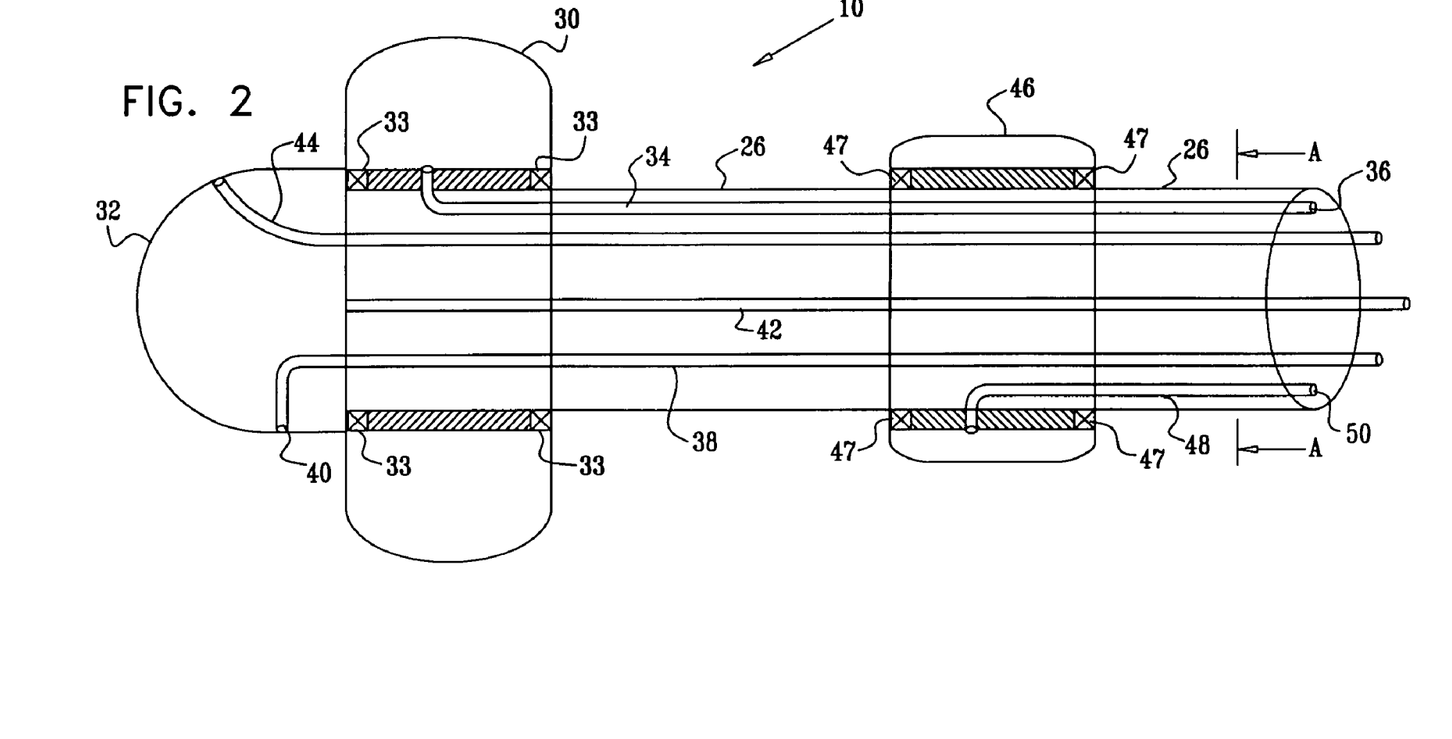
FIGS. 2 and 3 are simplified sectional illustrations of distal and proximal portions, respectively, of the system of FIG. 1.
Figure 3:
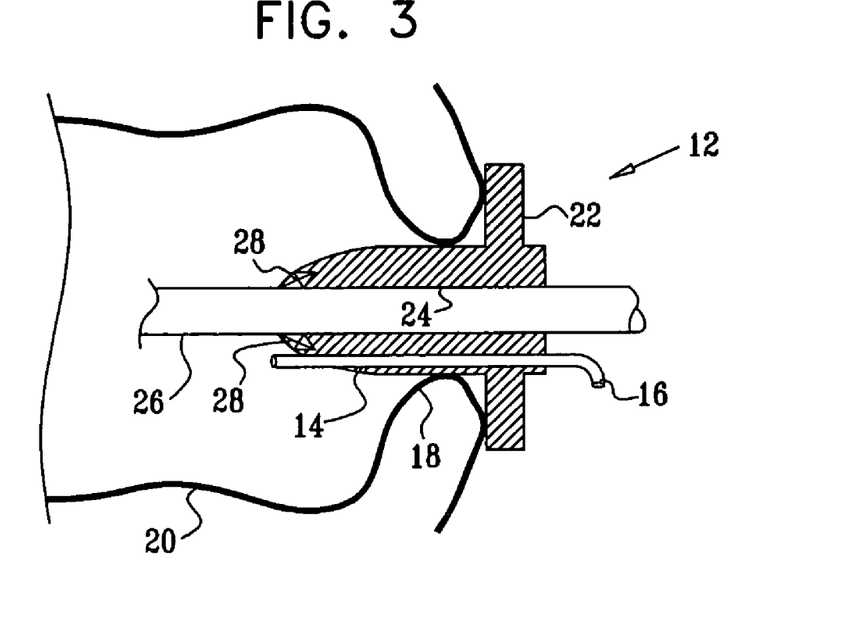
Figure 4:
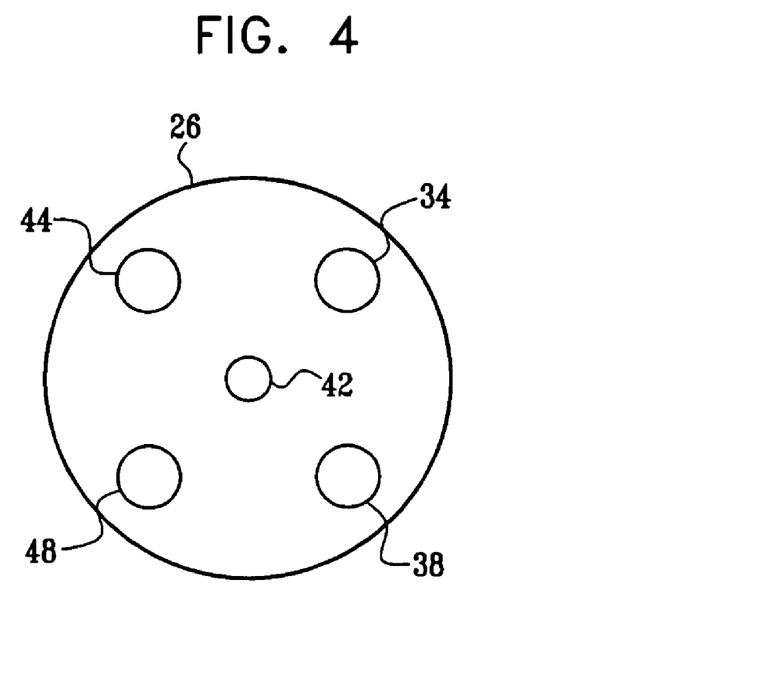
FIG. 4 is a simplified sectional illustration of a carrier of the system of FIG. 1, the section being taken transverse to a longitudinal axis of the carrier, in accordance with an embodiment of the present invention.

Reference is now made to FIGS. 1-3, which illustrate a system 10, constructed and operative in accordance with an embodiment of the present invention.

As seen best in FIG. 3, system 10 may include a guide member 12, which may be constructed of any medically safe material, such as but not limited to, plastic or metal. Guide member 12 may be formed with a first passageway 14 connected to a source 16 of a pressurized biologically-compatible fluid ("fluid pressure source 16"), such as but not limited to, a source of pressurized air, $CO_2$ or water. Guide member 12 may be at least partially insertable into a proximal opening 18 (e.g., the rectum) of a body lumen 20 (e.g., the colon). Guide member 12 may include an annular ring 22 for abutting against the proximal opening 18.

Guide member 12 may be formed with a bore 24 through which an elongate carrier 26 may be arranged for sliding movement. An O-ring 28 may be provided for dynamically sealing carrier 26 in its sliding motion relative to the guide member 12. Carrier 26 may be any slender wire, catheter or tube and the like, constructed of any medically safe material, such as but not limited to, a flexible plastic or metal. Carrier 26, including its tip, may be safely deflected and steered through body lumen 20.

A piston head 30 may be mounted on carrier 26. Piston head 30 may be inflatable, and as such may be constructed of any medically safe elastomeric material, such as but not limited to, a bladder or membrane made of polyurethane or silicone rubber, for example. An image-capturing device 32 may be mounted on carrier 26 distal to piston head 30. Piston head 30 is typically fixed to carrier 26 and sealed thereto with O-rings 33, but optionally may be arranged to slide on carrier 26 up to some distal stop which arrests further distal motion of piston head 30 (image-capturing device 32 may serve as the distal stop, for example). Image-capturing device 32 may comprise, without limitation, a camera (e.g., CCD or CMOS), or alternatively x-ray, ultrasonic, MRI, infrared and/or microwave imaging devices.

Other therapeutic or diagnostic devices may be mounted on or in carrier 26, such as but not limited to, a magnet, drug delivery devices (e.g., via iontophoresis), gene therapy devices and others.

Carrier 26 may include a second passageway 34 in fluid communication with piston head 30, connected to a source of fluid pressure 36 (e.g., pressurized air or water) for inflating piston head 30. For some applications, piston head-inflation fluid pressure source 36 is regulated to maintain a generally constant pressure within piston head 30, regardless of changes of volume of the piston head which occur in response to diameter changes of lumen 20.

A vent tube 38 may pass through or around piston head 30, having an opening 40 distal to piston head 30 through which fluid is ventable to the outside. That is, the proximal end of vent tube 38 vents the fluid past guide member 12 to the outside. For some applications, the proximal end of vent tube 38 may be connected to a suction source (not shown) for sucking fluid through vent tube 38. "Fluid," as used herein, includes liquids and gases.

In an embodiment, vent tube 38 is not used, but instead piston head 30 is temporarily deflated (at least in part), intermittently and/or in response to excess pressure accumulating distal to piston head 30. The temporary deflation of the piston head allows venting of the distal pressure to occur through passageway 14, typically in conjunction with a temporary decoupling of passageway 14 from fluid pressure source 16.

A power supply tube 42 (e.g., containing electrical wires, fiber optics, etc.) may pass through carrier 26, for connection to image-capturing device 32. Alternatively, the electrical and optical components of image-capturing device 32 may have their own internal power source, with no need for external wiring. Image-capturing device 32 may wirelessly transmit or receive data to or from an external processor (not shown). The components of system 10 may be fully automated with sensors and operate in a closed or open control loop.

A fluid supply tube 44 may pass through carrier 26, which may be connected to a fluid source (not shown), e.g., pressurized water, for cleaning the area near image-capturing device 32, or in combination with the vent tube 38, for cleaning body lumen 20 itself (e.g., the colon).

Experiments carried out by the inventors have shown that the system, as described hereinabove, is able to safely and efficiently advance a colonoscope through the colon of an anesthetized 90 kg pig. In these experiments, elongate carrier 26 was generally radio-opaque, and its motion was tracked in real-time using fluoroscopic imaging. Vent tube 38 was utilized, having an inner diameter of 2 mm. It acted passively (without being connected to a suction source), in order to allow pressure accumulating distal to piston head 30 to be vented to the outside.

In these experiments, a range of operating pressures were examined. The proximal pressure and the pressure within the piston head (intra-head pressure) were controlled, and values were recorded at which satisfactory movement of piston head 30 was observed. In general, for intra-head pressures ranging between 25 and 40 millibar, movement of piston head 30 was observed when the proximal pressure reached 30-100% of the intra-head pressure.

Typically, when the proximal pressure was below a threshold value, no movement was observed. As the proximal pressure was elevated above the threshold value, piston head 30 advanced through the colon. If the proximal pressure increased significantly above the threshold pressure (e.g., 2-10 millibar above the threshold pressure), then there was pressure leakage between piston head 30 and the wall of lumen 20, and advancement of piston head 30 ceased. In response to such a leak, the proximal pressure was lowered, vent tube 38 allowed the excess accumulated distal pressure to vent to the outside, and movement of piston head 30 recommenced.

In an experiment, an inflatable piston head was formed of thin silicone, and was shaped to have a distal lobe, a proximal lobe, and an intermediate portion connecting the distal and proximal lobes. (See FIGS. 10A and 10B.) For an intra-head pressure of 30 millibar, the piston head advanced through the colon when the proximal pressure was maintained between 10 and 20 millibar. During advancement of the piston head, vent tube 38 vented to the outside the pressure that accumulated due to the advancement of the piston head. Leakage around the piston head was observed for proximal pressures greater than about 20 millibar. For an intra-head pressure of 40 millibar, the piston head advanced through the colon when the proximal pressure was maintained between 27 and 30 millibar, both on straight and curved portions of the colon. For straight portions of the colon, proximal pressures of as low as 20 millibar were also sufficient to produce satisfactory movement of the piston head.

Although the rate of advance of the two-lobed piston head was found to vary with the selected pressures, in one experiment using a thin-walled two-lobed piston head, a total time of 2 minutes passed during the advancing of a colonoscope 1.5 meters into the colon of the pig. In another experiment, using a thick-walled two-lobed piston head, an intra-head pressure of 70 millibar and proximal pressure of 50 millibar resulted in 1.5 meters of colonoscope advancement in 1 minute 41 seconds. Thin-walled piston heads useful for these embodiments of the invention typically have a head wall thickness between 10 and 100 microns, e.g., 50 microns. Thick-walled piston heads useful for these embodiments of the invention typically have a head wall thickness greater than 100 microns, e.g., 150 microns, or 250 microns.

In another experiment, the piston head was formed of polyurethane, and was shaped like a cone, as described hereinbelow with reference to FIGS. 7-9. In this experiment, satisfactory advancement of the piston head was obtained at a proximal pressure of 35 millibar, when the intra-head pressure was also 35 millibar. The satisfactory advancement was obtained both on straight and curved portions of the colon.

It is noted that in these experiments, during the time when the intra-head pressure was kept constant, the volume of the piston head changed actively in response to changes in diameter of lumen 20.

Reference is now made to FIGS. 1, 2 and 5A-C, which illustrate operation of system 10, in accordance with an embodiment of the present invention. In this embodiment, an auxiliary piston head 46 may be mounted on the carrier proximal to distal piston head 30. Auxiliary piston head 46, which like piston head 30 may be inflatable, may be fixed axially to carrier 26 at a fixed distance from piston head 30. Auxiliary piston head 46 may be sealed with respect to carrier 26 with O-rings 47. Carrier 26 may include a third passageway 48 in fluid communication with auxiliary piston head 46, connected to a source of fluid pressure 50 for inflating auxiliary piston head 46.

System 10 may be inserted in the rectum with piston heads 30 and 46 initially deflated to facilitate insertion. Distal piston head 30 may then be gently inflated until it expands to the inner wall of body lumen 20. This configuration is shown in FIG. 1. Pressurized fluid (e.g., air) from fluid pressure source 16 may be introduced into the colon through the first passageway 14 of guide member 12. The pressurized fluid creates greater fluid pressure acting on the proximal side of piston head 30 than on the distal side of piston head 30. Opening 40 of vent tube 38 may assist in creating the pressure difference across piston head 30, either passively, or actively via applied suction. This pressure difference propels piston head 30 together with carrier 26 distally into the body lumen (in this example, the colon), as indicated by arrow 60. Image-capturing device 32 may capture images of body lumen 20 as system 10 travels therethrough.

Figures 5A, 5B:
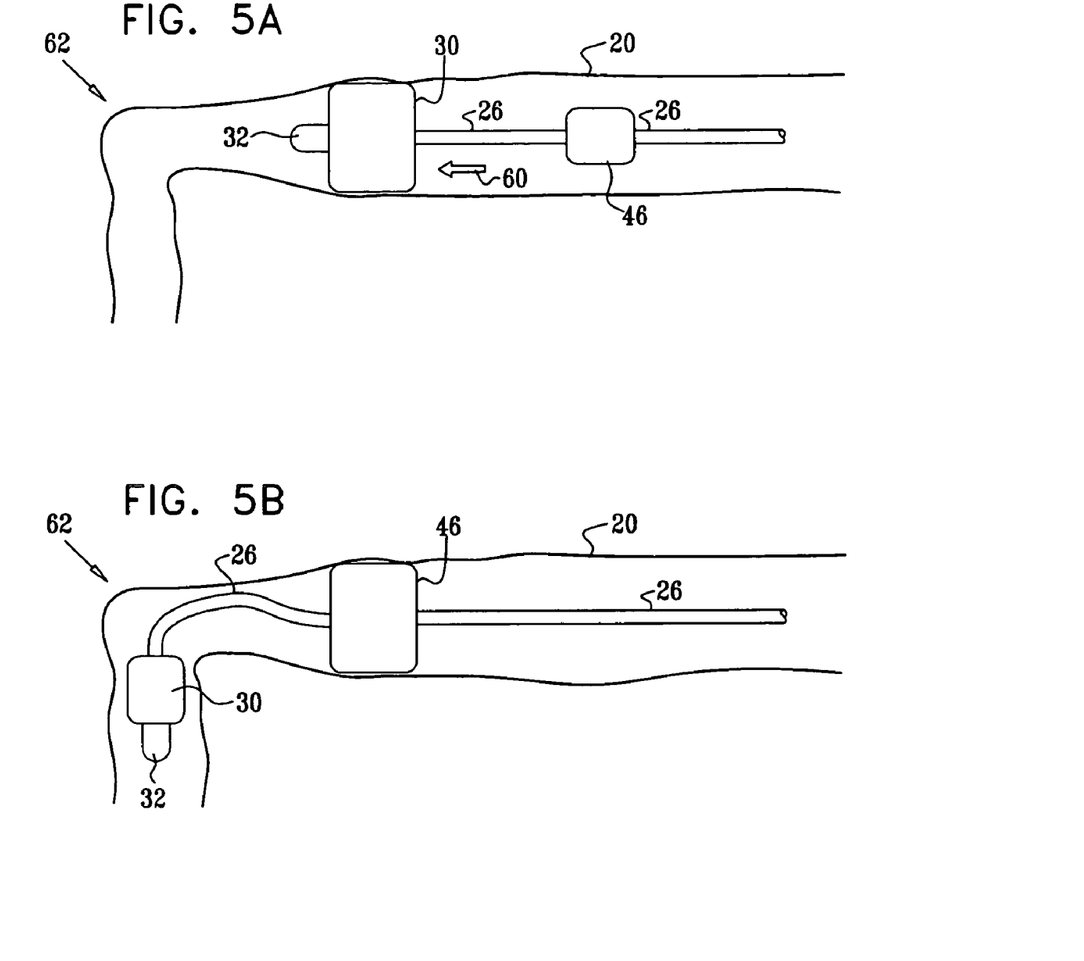
FIGS. 5A, 5B and 5C are simplified pictorial illustrations of the system of FIG. 1, showing three steps of a mode of operation thereof, wherein inflatable piston heads are inflated and deflated to negotiate obstacles in a body lumen, in accordance with an embodiment of the present invention.
Figure 5C:
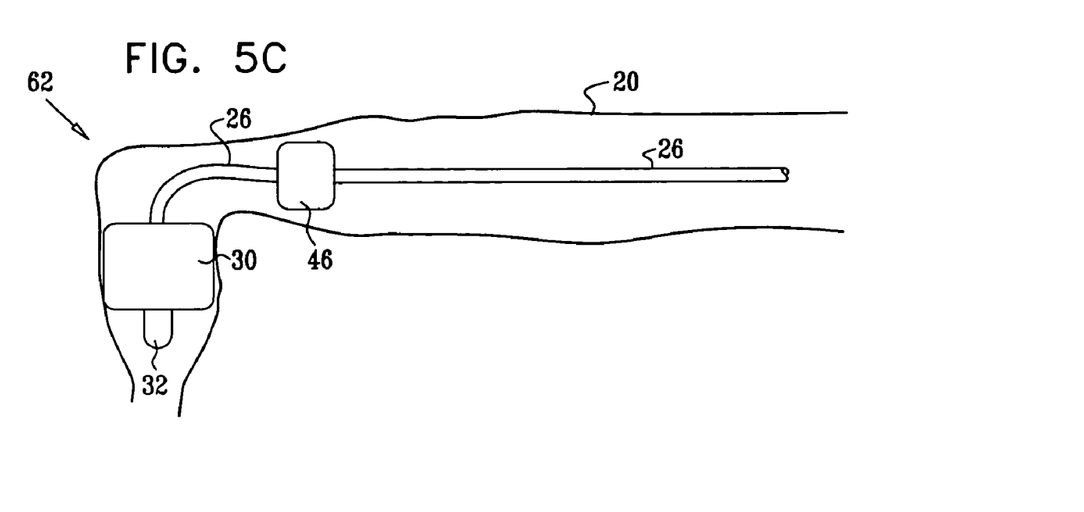

As seen in FIG. 5A, system 10 may eventually reach an obstacle or tight turn, indicated by arrow 62. In such a case, proximal piston head 46 may be inflated and distal piston head 30 may be deflated as shown in FIG. 5B. In this configuration, the pressurized fluid creates greater fluid pressure acting on the proximal side of proximal piston head 46 than on the distal side of proximal piston head 46. This pressure difference propels proximal piston head 46 together with carrier 26 distally, as indicated by arrow 64. This distal movement brings distal deflated piston head 30 past the obstacle, as seen in FIG. 5B. System 10 continues its distal movement in body lumen 20 until proximal piston head 46 reaches the obstacle. At this point, distal piston head 30 may be inflated and proximal piston head 46 may be deflated once again, as shown in FIG. 5C. Once again, the pressurized fluid creates greater fluid pressure acting on the proximal side of distal piston head 30 than on the distal side of distal piston head 30. The pressure difference propels system 10 distally in body lumen 20, and brings proximal deflated piston head 46 past the obstacle. The cycle may be repeated as often as necessary.

Figure 6:
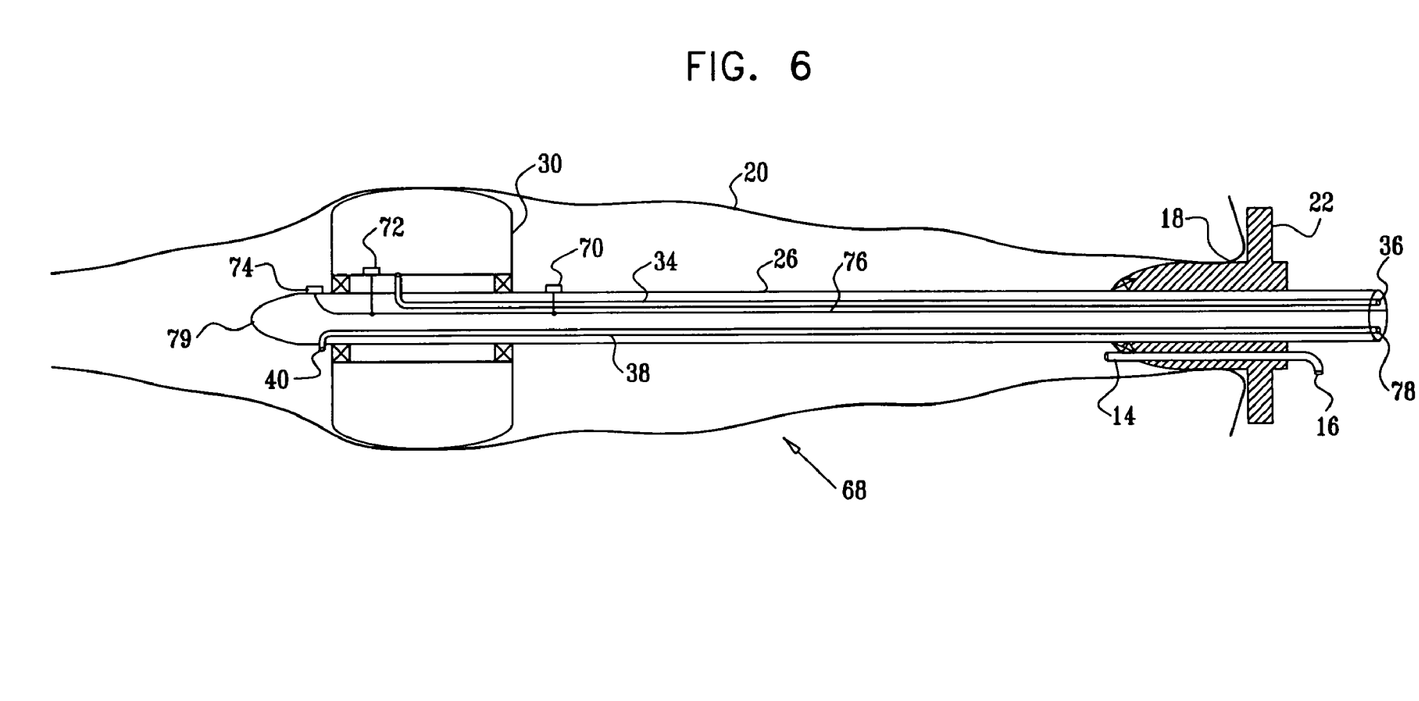
FIG. 6 is a pictorial illustration of a system for use in a body lumen, constructed and operative in accordance with an embodiment of the present invention.

Reference is now made to FIG. 6, which illustrates a system 68, constructed and operative in accordance with an embodiment of the present invention. System 68 operates in substantially the same manner as system 10, described hereinabove with reference to FIGS. 1-4, in that distal piston head 30 is inflated until it is in contact with body lumen 20, such that a seal between piston head 30 and lumen 20 is formed. Pressurized fluid is then introduced via first passageway 14, producing a larger pressure on the proximal face of piston head 30 than on the distal face of piston head 30, resulting in a net force acting to move piston head 30 distally. A sufficient net pressure force results in distal movement of piston head 30 along with elongate carrier 26 and a tool 79. Tool 79 may comprise an imaging device, a biopsy device, or other apparatus to be used in body lumen 20.

Additionally, for some applications of the present invention, a suction source 78 is coupled to opening 40 via vent tube 38 to provide suction on the distal face of piston head 30 and facilitate the distal movement of piston head 30. Providing suction at opening 40 may also be used in some applications to remove contents of the lumen, such as excess fluid or stool, that are impeding the movement of piston head 30. For some applications, the suction decreases an accumulation of gas distal to piston head 30 that may be uncomfortable for the patient.

System 68 typically comprises one or more pressure sensors, for example in order to be able to improve or optimize the performance of the system with respect to ease and speed of movement of system 68 through lumen 20. In particular, a first pressure sensor 70 is located proximal to distal piston head 30, in order to determine the pressure acting on the proximal face of distal piston 30. A second pressure sensor 72 is located inside distal piston head 30 to determine the inflation pressure of the distal piston head. A third pressure sensor 74 is located distal to distal piston head 30, to determine the pressure acting on the distal face of piston head 30. The three pressure sensors are coupled to a pressure sensor bus 76, such that the various pressure readings can be sent to an electromechanical or mechanical control unit (not shown), which regulates the different pressures, either automatically or with input from the operator of the system. For some applications, only one of the pressure sensors is included in system 68 (e.g., sensor 70, sensor 72, or sensor 74). For other applications, two of the pressure sensors are included, and one is omitted (e.g., sensor 70, sensor 72, or sensor 74).

In some embodiments of the present invention, satisfactory performance of system 68 is attained by maintaining a pressure on the proximal side of piston head 30 at about 25 millibar gauge, a pressure on the distal side of piston head 30 at about 5 millibar gauge, and a pressure inside piston head 30 at about 20 millibar gauge. These values typically range, as appropriate, between about +10 and +50 millibar, −5 and +15 millibar, and +10 and +60 millibar, respectively.

For some applications, during distal advancement of system 68, the pressure inside piston head 30 is maintained within about 5 millibar of the pressure differential across either side of piston head 30. For example, using the exemplary numbers cited above, a pressured differential across the piston head is 25 millibar−5 millibar=20 millibar. By maintaining the pressure inside piston head 30 within 5 millibar of the pressure differential, the pressure inside piston head 30 would generally remain between 15 and 25 millibar. The pressure within piston head 30 is typically maintained near this differential pressure when piston head 30 comprises a flexible but substantially non-elastic material (e.g., a material such as a polyurethane that stretches less than 10% during inflation at less than 50 millibar). For embodiments in which piston head 30 comprises a flexible and elastic material (e.g., a material comprising silicone that stretches more than 10% during inflation at less than 50 millibar), the pressure within piston head 30 is typically greater than the differential pressure.

Other combinations of the distal, proximal, and inside pressures for piston head 30 may be better suited for some applications, and the above numbers are not meant to limit the various operating pressures of embodiments of the current invention. Additionally, for some applications of the present invention, the various pressures acting on piston head 30 are regulated depending on where in the lumen the piston head is located.

To further ease the movement of piston head 30 in lumen 20, piston head 30 comprises a low friction coating, which acts to reduce the friction between piston head 30 and lumen 20. For example, piston head 30 may comprise a Teflon coating or other biocompatible low friction coating. Additionally or alternatively, the low friction coating comprises a suitable lubricant.

Although FIG. 6 only shows a distal piston head, it is to be understood that the scope of the present invention includes a system comprising a proximal piston head, as shown in FIG. 1, comprising the various pressure control and measuring apparatus described hereinabove with regard to distal piston head 30 of FIG. 6.

Figure 7:
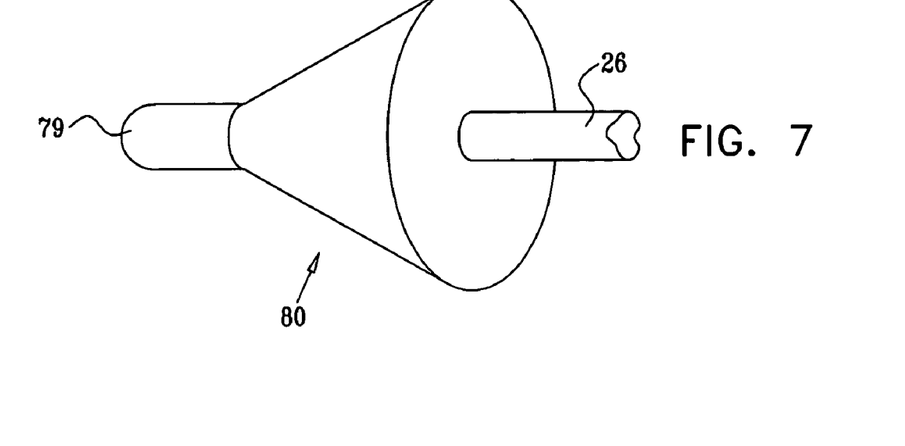
FIG. 7 is a pictorial illustration of an inflated conical balloon, which is adapted for use in accordance with an embodiment of the present invention.

Reference is now made to FIG. 7, which illustrates an inflatable piston head 80, constructed and operative in accordance with an embodiment of the present invention. Inflatable piston head 80 comprises an inflatable balloon that has the general form of a body of revolution about the axis formed by elongate carrier 26, wherein the distal end has a smaller diameter than the proximal end. Piston head 80 typically comprises a material that is flexible but substantially inelastic in the range of pressures typically encountered, such that the shape of the piston head is not substantially changed by elastic deformation when the piston head is inflated. Alternatively, piston head 80 comprises a flexible and elastic material. In some embodiments of the present invention, inflatable piston head 80 has the shape of a cone, as shown in FIG. 7. It is noted that whereas a cone is formed by rotating a straight line about an axis of revolution, other shapes for inflatable piston head 80 are formed by rotating curved lines about an axis of revolution. For example, a parabola or circular arc may be used to generate appropriate shapes. In the context of the present patent application and in the claims, all such shapes which become narrower towards their distal end are referred to as having a "distally-narrowing portion."

For some embodiments of the present invention, the base of inflatable piston head 80 is flat. In some other embodiments, the base of inflatable piston head 80 is curved, wherein the curvature may be either concave or convex.

Figure 8:
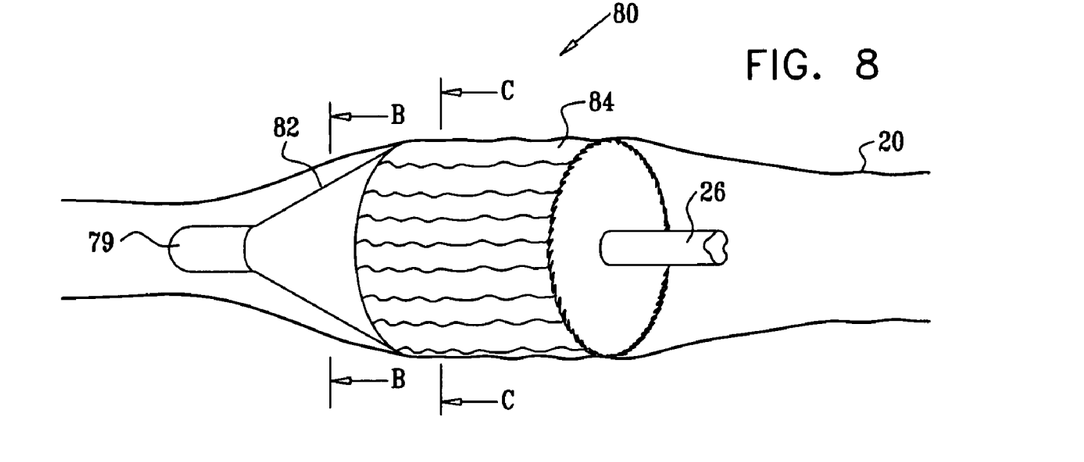
FIG. 8 is a pictorial illustration of a partially-inflated conical balloon in a body lumen, in accordance with an embodiment of the present invention.

FIG. 8 shows an application of inflatable piston head 80, in accordance with an embodiment of the present invention. Piston head 80 is typically inserted into lumen 20 in a deflated state and subsequently inflated until appropriate contact is made with the lumen. Due to the shape of inflatable piston head 80, most of a fully-inflated portion 82 of the piston head is not in substantial contact with lumen 20, while a partially-inflated portion 84 of the piston head is in contact with lumen 20, once the piston head is fully pressurized. A good seal between piston head 80 and lumen 20 is typically obtained where fully-inflated portion 82 meets partially-inflated portion 84.

Figure 9A:
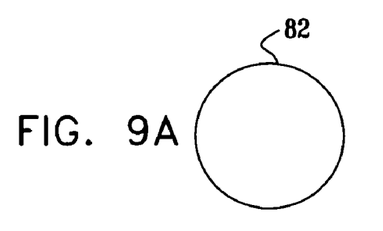
FIG. 9A is a pictorial illustration of the cross-section of a fully inflated portion of a conical balloon, in accordance with an embodiment of the present invention.
Figure 9B:
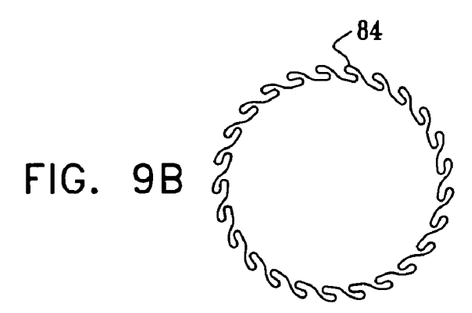
FIG. 9B is a pictorial illustration of the cross-section of a partially inflated portion of a conical balloon, in accordance with an embodiment of the present invention.

FIGS. 9A and 9B show cross-sections of the fully-inflated portion and the partially-inflated portion, respectively, in accordance with an embodiment of the present invention. Resistance of lumen 20 to radial expansion prevents the entire piston head from fully inflating (e.g., as shown in FIG. 7). Thus, partially-inflated portion 84 typically becomes somewhat wrinkled along the length of its contact with lumen 20.

Inflatable piston head 80 is regulated to respond to changes in the diameter of lumen 20 by inflating more as the lumen diameter increases, and by deflating as the lumen diameter decreases, all while maintaining satisfactory contact with the lumen. Since inflatable piston head 80 is typically made of a substantially inelastic material, a relatively modest pressure is needed to inflate the piston head. The inflation pressure is chosen to maintain an appropriate seal between the piston head and the lumen, without undue pressure on the lumen.

Figure 10A:
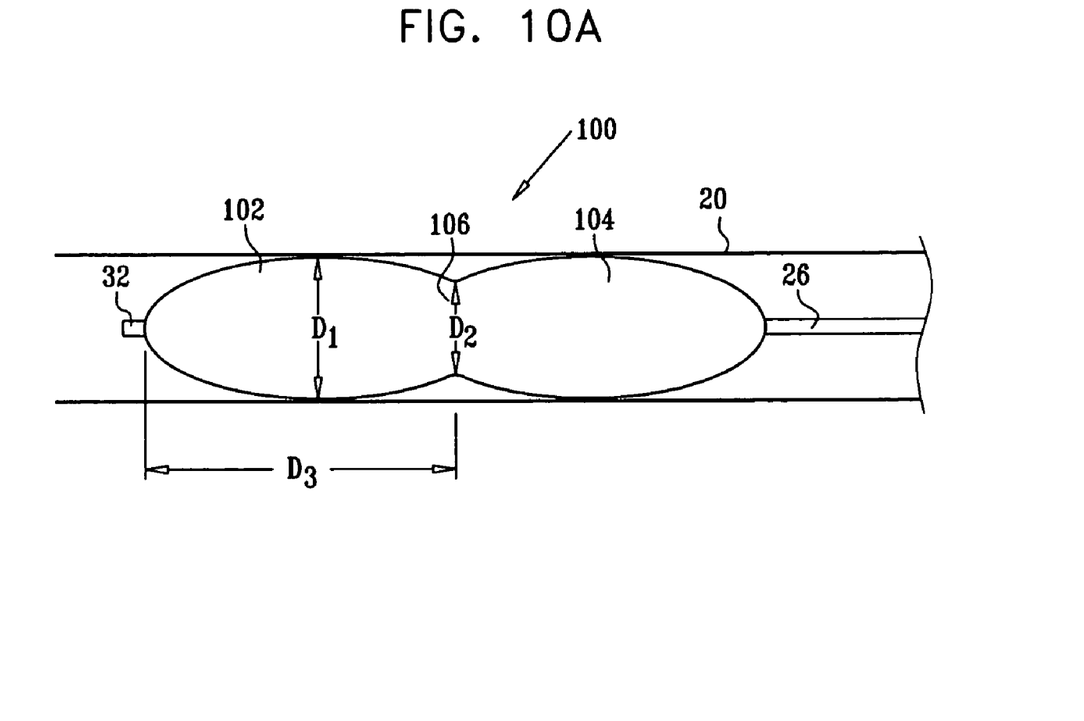
FIGS. 10A and 10B are pictorial illustrations of a system for use in a body lumen, constructed and operative in accordance with an embodiment of the present invention.
Figure 10B:
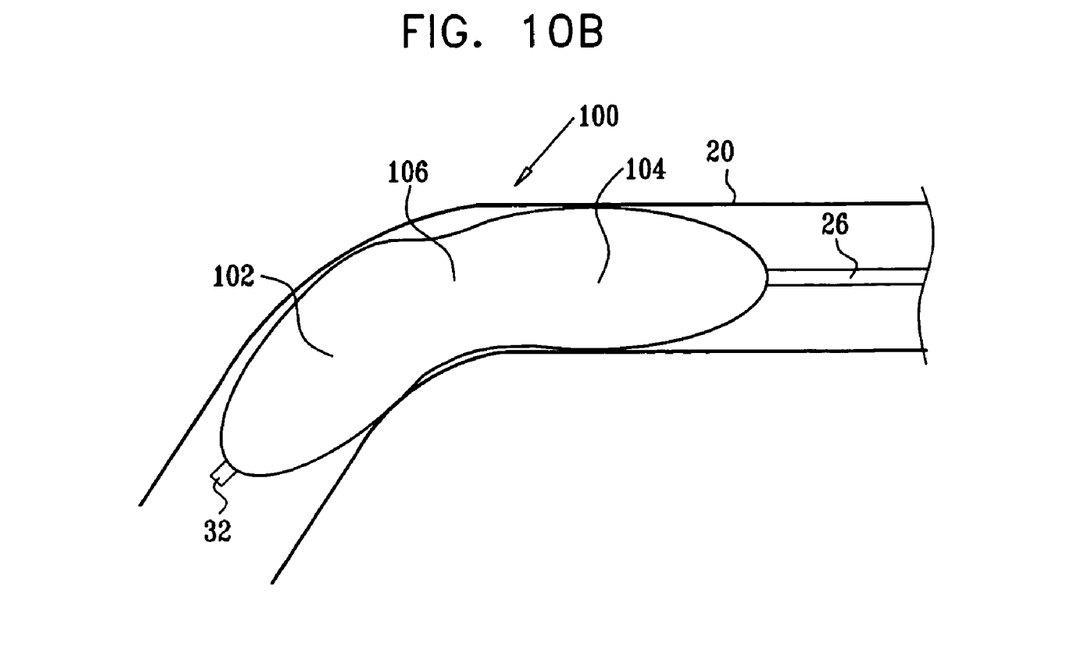

FIGS. 10A and 10B are pictorial illustrations of a multi-lobed piston head 100 for use in body lumen 20, constructed and operative in accordance with an embodiment of the present invention. Except for differences as noted, apparatus and techniques described hereinabove with respect to other piston heads are typically adapted for use with piston head 100.

Piston head 100 comprises a distal lobe 102 and a proximal lobe 104. Lobes 102 and 104 articulate at an intermediate portion 106. In an embodiment, dimensions of piston head 100 include: (a) a diameter D1 of distal lobe 102, which is substantially equal to the diameter of lumen 20, so as to make a satisfactory seal therewith, (b) a diameter D2 of intermediate portion 106, ranging from about 10% to 40% of D1, and (c) a length D3 of distal lobe 102, ranging from about 3 to 5 cm. It is noted that although multi-lobed piston head 100 only comprises two lobes, the scope of the present invention includes multi-lobed piston heads having more lobes (e.g., 3, 4, or 5 lobes).

Distal and proximal lobes 102 and 104 are in fluid communication with each other through intermediate portion 106. In steady state, as well as at the levels of movement typically encountered during advancement through the colon, the pressure within lobe 102 is substantially the same as the pressure within lobe 104. Thus, passageway 34 and fluid pressure source 36 (FIG. 2) regulate the pressure within both lobes substantially simultaneously. The diameters of the two lobes, however, typically vary independently, in response to changes in the shape of lumen 20 adjacent to each of the lobes. Typically, as with all of the inflatable piston heads described herein, fluid is actively added to or removed from the piston head to maintain a generally constant pressure within the piston head.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a biologically-compatible-fluid pressure source, comprising:
   an elongate carrier, adapted to be inserted through a proximal opening of a colon of a GI tract;
   an inflatable distal piston head coupled to a distal portion of the carrier and adapted to:
      be in direct contact with a wall of the colon when the carrier is inserted into the colon, by being inflated, so as to attain and maintain the direct contact with the wall of the colon,
      be advanced distally through the colon in response to pressure from the fluid pressure source impinging on a proximal side of the piston head, while the piston is in the inflated state, and
      facilitate passage of fluid out of the colon from a site within the colon distal to the piston head;
   a pressure sensor, adapted to measure a first pressure associated with operation of the apparatus; and
   a control unit, adapted to regulate a second pressure associated with operation of the apparatus responsive to the measurement of the pressure sensor.

2. The apparatus according to claim 1, wherein an outer surface of the piston head in contact with the wall of the colon comprises a low friction coating suitable for facilitating sliding of the piston head against the wall of the colon.

3. The apparatus according to claim 1, wherein the apparatus comprises a vent tube, and wherein the piston head is adapted to facilitate the passage of the fluid out of the colon through the vent tube.

4. The apparatus according to claim 3, wherein the vent tube is shaped to define an inner diameter thereof that is between 1 and 3 millimeters.

5. The apparatus according to claim 3, wherein the vent tube is adapted to passively permit the passage of the fluid out of the colon.

6. The apparatus according to claim 3, wherein the vent tube is adapted to be coupled to a suction source, whereby to actively facilitate the passage of the fluid out of the colon.

7. The apparatus according to claim 6, wherein the vent tube is adapted to be coupled to the suction source such that during operation of the apparatus, a pressure distal to the piston head is between −5 millibar and +15 millibar.

8. The apparatus according to claim 1, wherein the apparatus comprises an auxiliary piston head, coupled to the carrier at a position proximal to the distal piston head, wherein the auxiliary piston head is adapted to be inflated so as to attain and maintain direct contact with the wall of the colon, and wherein:
   (a) at least one time while the carrier is within the colon, the distal piston head is adapted to be in a state of being already deflated at least in part simultaneously with the auxiliary piston head being already inflated and being advanced distally through the colon in response to pressure from the fluid pressure source, and
   (b) at least one other time while the carrier is within the colon, the auxiliary piston head is adapted to be in a state of being already deflated at least in part simultaneously with the distal piston head being already inflated and being advanced distally through the colon in response to pressure from the fluid pressure source.

9. The apparatus according to claim 1, wherein the piston head is adapted to be intermittently deflated at least in part, while in the colon, whereby to facilitate the passage of the fluid out of the colon from the site within the colon distal to the piston head.

10. The apparatus according to claim 1, wherein the piston head is adapted to be at an inflation pressure between 10 and 60 millibar during advancement through the colon.

11. The apparatus according to claim 10, wherein the piston head is adapted to advance through the colon in response to a pressure from the fluid pressure source that is between 30% and 100% of the inflation pressure.

12. The apparatus according to claim 11, wherein the piston head is adapted to advance through the colon in response to a pressure from the fluid pressure source that is between 50% and 100% of the inflation pressure.

13. The apparatus according to claim 10, wherein the piston head is adapted to be at an inflation pressure between 20 and 50 millibar during advancement through the colon.

14. The apparatus according to claim 13, wherein the piston head is adapted to be at an inflation pressure between 30 and 45 millibar during advancement through the colon.

15. The apparatus according to claim 14, wherein the piston head is adapted to advance through the colon in response to a pressure from the fluid pressure source that is between 30% and 100% of the inflation pressure.

16. The apparatus according to claim 15, wherein the piston head is adapted to advance through the colon in response to a pressure from the fluid pressure source that is between 50% and 100% of the inflation pressure.

17. The apparatus according to claim 16, wherein the piston head is adapted to advance through the colon in response to a pressure from the fluid pressure source that is between 50% and 80% of the inflation pressure.

18. A method, comprising:
   placing into a body lumen of a subject an inflatable distal piston head that is coupled to an elongate carrier;
   gutting the inflatable distal piston head in direct contact with a wall of the body lumen by inflating the piston head;
   advancing the piston head distally through the body lumen by conveying fluid pressure from a site outside of the subject to an external proximal surface of the distal piston head; and
   facilitating passage of fluid out of the lumen from a site within the lumen distal to the piston head.

19. The method according to claim 18, comprising applying a low friction coating to an outer surface of the piston head intended for contact with the wall of the lumen, the low friction coating being suitable for facilitating sliding of the piston head against the wall of the lumen.

20. The method according to claim 18, wherein the lumen includes a gastrointestinal (GI) tract, and wherein placing the piston head comprises placing the piston head in direct contact with a wall of the GI tract.

21. The method according to claim 20, wherein the GI tract includes a colon, and wherein placing the piston head includes placing the piston head in direct contact with a wall of the colon.

22. The method according to claim 21, wherein facilitating the passage of the fluid comprises facilitating the passage of the fluid out of the lumen through a vent tube extending from the site distal to the piston head to a site outside of the lumen.

23. The method according to claim 22, wherein facilitating the passage of the fluid comprises passively permitting the passage of the fluid through the vent tube and out of the lumen.

24. The method according to claim 22, wherein facilitating the passage of the fluid comprises actively removing the fluid from the lumen.

25. The method according to claim 24, wherein actively removing the fluid comprises applying to the site distal to the piston head a pressure between −5 millibar and +15 millibar.

26. The method according to claim 21, wherein placing the piston head in direct contact with the wall comprises inflating the piston head to an extent sufficient to attain and maintain the direct contact with the wall of the colon.

27. The method according to claim 26, wherein the method comprises:
   placing an auxiliary piston head proximal to the distal piston head;
   inflating the auxiliary piston head to an extent sufficient to attain and maintain direct contact with the wall of the colon;
   at least one time while the distal piston head is within the body lumen, deflating the distal piston head at least in part, such that at a post-distal-piston-head-deflation time when the distal piston head is in a state of being already deflated at least in part, the auxiliary piston head is inflated and advancing distally through the colon in response to the applied fluid pressure; and
   at least one other time while the distal piston head is within the body lumen, deflating the auxiliary piston head at least in part, such that at a post-auxiliary-piston-head-deflation time when the auxiliary piston head is in a state of being already deflated at least in part, the distal piston head is inflated and advancing distally through the colon in response to the applied pressure.

28. The method according to claim 26, wherein facilitating the passage of the fluid out of the lumen comprises intermittently deflating the piston head at least in part.

29. The method according to claim 26, wherein inflating the piston head comprises inflating the piston head at an inflation pressure between 10 and 60 millibar.

30. The method according to claim 29, wherein applying the fluid pressure comprises setting the fluid pressure to between 30% and 100% of the inflation pressure.

31. The method according to claim 30, wherein applying the fluid pressure comprises setting the fluid pressure to between 50% and 100% of the inflation pressure.

32. The method according to claim 29, wherein inflating the piston head comprises inflating the piston head at an inflation pressure between 20 and 50 millibar.

33. The method according to claim 32, wherein inflating the piston head comprises inflating the piston head at an inflation pressure between 30 and 45 millibar.

34. The method according to claim 33, wherein applying the fluid pressure comprises setting the fluid pressure to between 30% and 100% of the inflation pressure.

35. The method according to claim 34, wherein applying the fluid pressure comprises setting the fluid pressure to between 50% and 100% of the inflation pressure.

36. The method according to claim 35, wherein applying the fluid pressure comprises setting the fluid pressure to between 50% and 80% of the inflation pressure.

* * * * *